United States Patent [19]

Wiesehahn

[11] Patent Number: 4,748,120

[45] Date of Patent: * May 31, 1988

[54] PHOTOCHEMICAL DECONTAMINATION TREATMENT OF WHOLE BLOOD OR BLOOD COMPONENTS

[75] Inventor: Gary P. Wiesehahn, Alameda, Calif.

[73] Assignee: Diamond Scientific Co., Des Moines, Iowa

[ * ] Notice: The portion of the term of this patent subsequent to Feb. 23, 2005 has been disclaimed.

[21] Appl. No.: 928,841

[22] Filed: Oct. 20, 1986

Related U.S. Application Data

[63] Continuation of Ser. No. 490,681, May 2, 1983, abandoned.

[51] Int. Cl.$^4$ ............ C12N 13/00; A61K 39/00; A61K 35/14; A61K 35/48
[52] U.S. Cl. ............... 435/173; 424/85; 424/89; 424/90; 424/101; 514/2; 514/6; 530/380; 530/381; 530/383; 530/387; 530/389; 530/829
[58] Field of Search .......... 435/172.1, 173, 183, 435/188, 236, 238, 269, 800, 814; 424/89, 90, 101, 85; 514/2; 530/350, 363, 380–388, 412–414, 427

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 546/270 |
| 4,321,919 | 3/1982 | Edelson | 128/214 R |

OTHER PUBLICATIONS

Musajo et al, *Experentia*, vol. XXI, pp. 22–24, "Photosensitizing Furocoumanns: Interaction with DNA and Photo-Inactivation of DNA Containing Viruses".

Veronese et al, *Photochem Photobiol*, vol. 36, pp. 25–30, "Photoinactivation of Enzymes by Linear and Angular Furocoumanns".

De Mol et al., *Chem. Abst.*, vol. 95, No. 74462k, p. 197, 1981, "On the Involvement of Singlet Oxygen in Mutation Induction by 8-Methoxypsoraten and UVA Radiation in *Escherichia coli* K-12".

De Mol et al, *Photochem Photobiol*, vol. 33, pp. 815–819, 1981, "Relation Between Some Photobiological Properties of Furocoumanns and their Extent of Singlet Oxygen Formation".

deMol et al. (1981) Photochem. Photobiol. 34:661–666.

Joshi and Pathak (1983) Biochem. Biophys. Res. Comm., 112:638–646.

Grossweiner (1982) NCI Monograph, No. 66, 47–54.

Rodighiero and Dall'Acqua (1982) NCI Monograph, No. 66, 31–40.

*Primary Examiner*—Thomas G. Wiseman
*Assistant Examiner*—Robin Lyn Teskin
*Attorney, Agent, or Firm*—Zarley, McKee, Thomte, Voorhees & Sease

[57] ABSTRACT

Biological compositions are freed of functional polynucleotides by treatment of the biological composition with psoralen derivatives under irradiation conditions in which the proteins retain their original physiological activities and any polynucleotide present is rendered inactive.

32 Claims, No Drawings

PHOTOCHEMICAL DECONTAMINATION TREATMENT OF WHOLE BLOOD OR BLOOD COMPONENTS

This is a continuation of application Ser. No. 490,681, filed May 2, 1983, now abandoned.

BACKGROUND OF THE INVENTION

1. Field of the Invention

Recipients of blood and blood components risk acquiring infections from foreign biological organisms, either pre-existing in the blood at the time of collection or transmitted to the blood product during manipulation. Medical personnel who are in contact with collected human blood or clinical samples also have a significant chance of being exposed to potentially lethal blood-borne or sample-borne biological organisms. Blood components today are obtained from blood donors and frequently involve pooled lots, where one or more of the donors may be harboring a viral, bacterial or other infection. Since the blood or blood components are required to provide physiological functions in a mammalian host, normally a human host, these functions must not be impaired by the decontamination treatment of the biological composition. In addition, the blood or blood components may not be modified in such a way as to make them immunogenic which could result in an adverse immune response. Finally, any treatment should not leave residues or products detrimental to the health of the host or such residues or products should be readily removable.

2. Description of the Prior Art

U.S. Pat. No. 4,327,086 describes the method for heat treating an aqueous solution containing human blood coagulation factor XIII. U.S. Pat. No. 4,321,919 proposes extracorporeal treatment of human blood with 8-methoxypsoralen (8-MOP). Hyde and Hearst, Biochemistry (1978) 17:1251–1257, describe the binding of two psoralen derivatives to DNA and chromatin. Musajo et al., Experientia (1965) XXI, 22–24, describe photo-inactivation of DNA-containing viruses with photosensitizing furocoumarins. U.S. Pat. Nos. 4,350,594, 4,348,283 and 4,350,156 describe filtration methods for selective removal of blood components based on molecular weight. U.S. Pat. No. 4,329,986 describes extracorporeal treatment of blood with a chemotherapeutic agent which is subsequently removed by dialysis. The July/August 1982 issue of Genetic Engineering News proposed the use of psoralens to sterilize "clinical or commercial reagents or instruments."

Some data showing substantial impairment of the biological function of certain enzyme proteins using furocoumarins are published in the scientific literature (see for example, Veronese, F. M. et al., Photochem. Photobiol. 34: 351 (1981); Veronese, F. M. et al., Photochem. Photobiol. 36: 25 (1982)).

SUMMARY OF THE INVENTION

Methods and compositions are provided for decontamination of biological compositions, permanently inactivating polynucleotides capable of having pathological effect in a mammalian host. Particularly, furocoumarin compositions are employed for inactivating polynucleotides, such as viral genomes, capable of infectious replication in a mammalian host. Compositions for use in a mammalian host may be decontaminated by treatment with furocoumarins and long wavelength ultraviolet (UVA) light.

DESCRIPTION OF THE SPECIFIC EMBODIMENTS

In accordance with the subject invention, compositions to be employed with mammalian hosts, which may harbor polynucleotides capable of detrimental physiological effects in a host, are combined with furocoumarin compositions and treated with UVA light under predetermined conditions, whereby the physiological activities of the non-nucleic acid components are retained. (Whenever the term "polynucleotide" is used in this application it should be understood to mean: (1) microorganisms containing nucleic acids (either DNA or RNA), (2) nucleic acid genomes or sub-genomic fragments from microorganisms, from procaryotes (lower life forms) or from eucaryotes (higher life forms), or (3) any other nucleic acid fragments.)

In decontaminating the biological composition, an aqueous medium containing the biological preparation is combined with an appropriate amount of the furocoumarin composition and irradiated with ultraviolet light under conditions where all of the polynucleotide is inactivated, while the components other than nucleic acid retain their normal physiological activities.

Various biological compositions may be employed, particularly protein compositions involving blood or blood components. Whole blood, packed red cells, platelets, and plasma (fresh or fresh frozen plasma) are of interest. Other blood components of interest include plasma protein portion, antihemophilic factor (AHF, Factor VIII); Factor IX and Factor IX complex (Factors II, VII, IX and X); fibrinogens, Factor XIII, prothrombin and thrombin (Factor II and IIa); immunoglobulins (e.g. IgA, IgD, IgE, IgG and IgM and fragments thereof e.g. Fab, F(ab')$_2$, Fc); hyper-immune globulins as used against tetanus and hepatitis B; cryoprecipitate; albumin; interferons; lymphokines; transfer factors; etc. Other biological compositions include vaccines, recombinant DNA produced proteins, oligopeptide ligands, etc. The protein concentration in the aqueous medium will generally range from about 1 $\mu$g/ml to 500 mg/ml, more usually from about 1 mg/ml to 100 mg/ml. The pH will normally be close to physiologic pH ($\sim$7.4), generally in the range of about 6 to 9, more usually about 7. Other components may be present in the medium, such as salts, additives, buffers, stabilizers, or the like. These components will be conventional components, which will be added for specific functions.

The furocoumarins will include psoralen and derivatives, where the substituents will be: alkyl, particularly of from 1 to 3 carbon atoms, e.g. methyl; alkoxy, particularly of from 1 to 3 carbon atoms, e.g. methoxy; and substituted alkyl, of 1 to 6, more usually 1 to 3 carbon atoms having from 1 to 2 heteroatoms, which will be oxy, particularly hydroxy or alkoxy of from 1 to 3 carbon atoms, e.g. hydroxymethyl and methoxymethyl, or amino, including mono- and dialkyl amino having a total of from 1 to 6 carbon atoms, e.g. aminomethyl. There will be from 1 to 5, usually 2 to 4 substituents, which will normally be at the 4, 5, 8, 4' and 5' positions, particularly at the 4'-position. Illustrative compounds include 5-methoxypsoralen, 8-methoxypsoralen (8-MOP), 4, 5',8-trimethylpsoralen (TMP), 4'-hydroxymethyl-4,5'8-trimethylpsoralen (HMT), 4'-aminomethyl-4,5',8-trimethylpsoralen (AMT), 4-methylpsoralen, 4,4'-dimethylpsoralen, 4,5'-dimethylpsoralen, 4',8-dimethylpsoralen, and 4'-methoxymethyl-4,5',8-trimethylpsoralen.

The subject furocoumarins are active with a wide variety of viruses and other polynucleotides, DNA or RNA, whether single stranded or double stranded. Illustrative viruses include: adenovirus, arenavirus, bacteriophage, bunyavirus, herpesvirus, orthomyxovirus, papovavirus, paramyxovirus, picornavirus, poxvirus, reovirus, retrovirus, rhabdovirus, and togavirus. Additional pathogenic microorganisms include bacteria, chlamydia, mycoplasma, protozoa, rickettsia and other unicellular microorganisms. Furocoumarins may also be effective in inactivating Hepatitis B and Non-A Non-B Hepatitis viruses. This inactivation method may also be used against uncharacterized infectious agents which may contain nucleic acid (such as the agent which causes Acquired Immune Deficiency Syndrome).

In addition to the furocoumarins, additives may be included which scavenge for singlet oxygen or other highly reactive oxygen containing species. Such additives include ascorbate, glutathione, sodium thionite, etc. In some instances these additives may have adverse effects, so that in each instance, their use will be determined empirically. Where such additives are present, they will be present in amounts ranging from about 20 $\mu g$ to 20 mg per ml.

The furocoumarins may be used individually or in combination, preferably in combination. Each of the furocoumarins may be present in amounts ranging from about 0.01 $\mu g$/ml to 1 mg/ml, preferably from about 0.5 $\mu g$/ml to 100 $\mu g$/ml, there not being less than about 1 $\mu g$/ml nor more than about 1 mg/ml of furocoumarins. For RNA, the preferred furocoumarins are AMT and HMT. For DNA, the preferred furocoumarin is TMP. For mixtures of DNA- and RNA-containing polynucleotides, or for inactivation of infectious agents or possibly infectious agents of unknown or uncertain nucleic acid classification, or for protection against infections of unknown etiology, preferably TMP and AMT are used in combination.

In carrying out the invention, the furocoumarins may be added to the biological composition by any convenient means in a manner substantially assuring the uniform distribution of the furocoumarins in the composition. The composition may then be irradiated under conditions ensuring that the entire composition is exposed to sufficient irradiation, so that the furocoumarins may react with any polynucleotide present to inactivate the polynucleotide. Depending upon the nature of the medium, particularly its opacity, as in the case of blood, the depth of the solution subject to irradiation will vary widely. Usually, the depth will be not less than about 0.025 millimeter, but may be a centimeter or more. With whole blood, the depth will generally range from about 0.025 millimeter to 2.5 millimeters. The light which is employed will generally have a wavelength in the range of about 300 nm to 400 nm. The intensity will generally range from about 0.1 mW/cm$^2$ to about 5 W/cm$^2$. In order to prevent denaturation, the temperature should be maintained below about 60° C., preferably below about 40° C., usually from about −10° C. to 30° C. The medium being irradiated may be irradiated while still, stirred or circulated, and may either be continuously irradiated or be subject to alternating periods of irradiation and non-irradiation. The circulation may be in a closed loop system or it may be in a single pass system ensuring that all of the sample has been exposed to irradiation. The total time for irradiation will vary depending upon the nature of the sample, the furocoumarin derivative used, the intensity and spectral output of the light source and the nature of the polynucleotides which may be present. Usually, the time will be at least 1 min. and not more than about 6 hrs., more usually from about 15 mins. to about 2 hrs. When circulating the solution, the rate of flow will generally be in the range of about 0.1 ml/min to 50 liters/min. It may be desirable to remove the unexpended psoralen and/or its photobreakdown products from the irradiation mixture. This can be readily accomplished by dialysis across an appropriately sized membrane or through an appropriately sized hollow fiber system after completion of the irradiation. It may be desirable in certain applications to remove bound or unbound furocoumarins using antibodies, including monoclonal antibodies, either in solution or attached to a substrate.

The following examples are offered by way of illustration and not by way of limitation.

EXPERIMENTAL

The following experiments were performed in order to demonstrate the ability of the psoralen photoreaction to destroy microbial contaminants contained in whole blood and blood products.

(1) Feline rhinotracheitis virus, a member of the herpesvirus family, was added to heparinized whole rabbit blood in an amount that would give a final concentration of approximately $2 \times 10^7$ PFU/ml. 4'-hydroxymethyl-4,5',8-trimethylpsoralen (HMT) was added to a portion of the rabbit blood and aliquots were irradiated for various periods of time. To test for remaining live virus, duplicate plaque assays were performed using cultured feline cells (Fc3Tg) (ATCC CCL 176), with a methylcellulose overlay. Virus titers were obtained as the arithmetical mean of viral plaques observed in duplication assay cultures 72 hours after exposure to test samples. The results are as follows:

The blood aliquot that received HMT only and no irradiation gave a titer of $5.3 \times 10^6$ PFU/ml. The aliquot that received HMT and five minutes of irradiation exhibited a titer of $4.5 \times 10^6$ PFU/ml. In the aliquot that received psoralen plus one hour of irradiation there was no detectable live virus remaining. The sensitivity of this assay should have permitted detection of residual virus at titers $\geq 1.0 \times 10^1$ PFU/ml. A blood sample which had received HMT and one hour of irradiation also showed no apparent damage to the red blood cells as judged by phase contrast microscope analysis and by absence of visible hemolysis. These data therefore demonstrate that high virus titers present in whole blood can be inactivated by psoralen plus light treatment which leaves the red cell component of the blood intact.

(2) In the second experiment Blue Tongue Virus (Serotype 11), a member of the reovirus family, and Feline Rhinotracheitis Virus, and Simian Virus 40 were added to a solution of Profilate (a commercial preparation of human clotting factor VIII produced by Alpha Therapeutics). The lyophilized preparation of Profilate (180 units) was dissolved in 10 ml of sterile water included with the commercial preparation. This solution was further diluted with barbital buffer (11.75 g sodium barbital and 14.67 g NaCl dissolved in 2 liters of de-ionized water and filtered through a 0.22 micron filter) to a final concentration of 5 units per milliliter. One portion (2 ml) was set aside at room temperature in the dark. This was sample 190 1. A second 2 ml portion was pumped through the apparatus described below for 1 hour with irradiation. This was sample #2. Through addition of appropriate amounts of reagents a third 2 ml portion was adjusted to contain 10 μg/ml AMT and 10 μg/ml HMT and was also irradiated for 1 hour. This was sample #3. The fourth 2 ml portion was adjusted to 10 μg/ml AMT, 10 μg/ml HMT, and 10 mM sodium ascorbate and was also irradiated for 1 hour. This was sample #4. All the samples were kept at 20° C. throughout the manipulations. The total elapsed time from dissolving of the lyophilized preparation to the completion of the clotting factor VIII assays was 6 and one-half hours.

The clotting factor VIII assays were performed at a variety of dilutions (ranging from 1:5 to 1:100) for each sample and were compared with the activity in normal human serum and with pooled normal human serum. The results are summarized in Table 1.

TABLE 1
Effect of Photochemical Inactivation Procedure and Its Components* on in vitro Activity of Factor VIII+

| dilution | normal | pool | Sample #1 $F^-$, $UVA^-$ | Sample #2 $F^-$, $UVA^+$ | Sample #3 $F^+$, $UVA^+$ |
|---|---|---|---|---|---|
| 1:5 | 97 | 108 | 225 | 150 | 186 |
| 1:10 | 102 | 102 | 245 | 155 | 186 |
| 1:20 | 93 | 92 | 280 | 176 | 196 |
| 1:50 | 101 | 95 | 265 | 190 | 232 |
| 1:100 | — | 100 | 255 | 196 | 263 |
| Average | 98 | 99 | 254 | 173 | 213 |

*F = Furocoumarin;
UVA = long wavelength ultraviolet light;
+Factor VIII activity expressed in % of normal activity.
100% = 1U/ml of Factor VIII activity The sample that was subjected to the psoralen inactivation protocol (sample #3) retained 84% of the factor VIII activity that was present in the control sample (#1). This was higher than the product activity retained by the sample that was only irradiated (68% retained for sample #2) and indicates that the psoralen photochemistry has little or no effect on the activity of factor VIII.

Samples otherwise identical to samples 1, 2, and 3 above were seeded with $2 \times 10^6$ PFU/ml of Feline Rhinotracheitis Virus (FeRT), $1 \times 10^7$ PFU/ml of Blue Tongue Virus (BTV), and $4 \times 10^8$ PFU/ml of Simian Virus 40 (SV-40). Table 2 shows the results of the plaque assays on those samples.

TABLE 2
Effect of Photochemical Inactivation Procedure and its Components* on Infectivity of Virus in Factor VIII preparation.+

| | Sample 1 $F^-$, $UVA^-$ | Sample 2 $F^-$, $UVA^+$ | Sample 3 $F^+$, $UVA^+$ |
|---|---|---|---|
| FeRT Titer | $8.6 \times 10^5$ | $3.5 \times 10^5$ | 0.0 |
| BTV Titer | $3.8 \times 10^7$ | $1.4 \times 10^7$ | $1.1 \times 10^2$ |
| SV-40 Titer | $2.5 \times 10^8$ | $1.6 \times 10^8$ | $1.2 \times 10^3$ |

*F = Furocoumarin;
UVA = long wavelength ultraviolet light.
+Infectivity determined by plaque assays in tissue culture.

In the case of FeRT the number of detectable virus particles was reduced by more than five orders of magnitude to beneath the limit of detection in the plaque assay. The BTV infectivity was reduced by about five orders of magnitude to 110 PFU/ml. The SV40 infectivity was reduced to a titer of $1.2 \times 10^3$. Thus, it is shown that multiple, widely distinct types of virus can be simultaneously inactivated by at least five orders of magnitude in the presence of factor VIII, using the simple, convenient, brief process described above, with retention of at least 84% of factor VIII activity. Based on the above observations, it is predictable that by extending, repeating or modifying the treatment, the probability of an infectious virus particle remaining can be reduced to an arbitrarily low value. In this manner suitable safety margins can be achieved for any of the cited applications.

APPARATUS AND SYSTEM

Since whole blood exhibits very high optical density for longwave UV light (absorption is high for visible light in the 400 nm to 500 nm range), the blood was irradiated through a suitably short optical path length. In this experiment blood was pumped through polyethylene capillary tubing of 0.875 millimeter inside diameter. The tubing was coiled around a 1.27 centimeter diameter tube and immersed in water which was maintained at 18° C. The blood was continuously circulated through the tubing by means of a peristaltic pump. The blood required approximately 2.5 minutes for a complete cycle through the capillary tubing and was in the light beam for approximately 20% of the stated irradiation time. The light source was a low pressure mercury lamp filtered through a cobalt glass filter. The filter transmit light of approximately 320 nm–380 nm, with peak transmittance at 360 nm. The incident intensity at the sample was approximately 40 mW/cm$^2$.

It is evident from the above results, and in accordance with the subject invention, that polynucleotides in biochemical compositions can be inactivated to provide a safe composition for administration to a mammalian host. The proteins present in the composition retain their physiological activity, so that they can fulfill their physiological function in a mammalian host. The method is simple, rapid, and can be expanded to treat large samples. The small amount of chemical reagent required will not generally be harmful to the host.

Although the foregoing invention has been described in some detail by way of illustration and example for purposes of clarity of understanding, it will be obvious that certain changes and modifications may be practiced within the scope of the appended claims.

What is claimed is:

1. A method for decontaminating blood components suspected of containing viruses, said blood components being selected from the group consisting of red blood cells, platelets, blood clotting factors, plasma and immunoglobulins, without substantial impairment of the physiological activities of the treated blood components, said method comprising:
   (a) adding to a blood component selected from the group consisting of red blood cells, platelets, blood clotting factors, plasma and immunoglobulins at least one psoralen compound in an amount sufficient to inactivate substantially all contaminating viruses prevent; and thereafter
   (b) irradiating said psoralen treated blood component with long wavelength ultraviolet light under operating conditions which maintain the concentrations of reactive oxygen species at levels which do not substantially impair the physiological activity of the treated blood component, and wherein said irradiation is conducted for a time sufficient to inactivate substantially all contaminating viruses present.

2. A method according to claim 1 wherein the conditions which maintain the concentration of reactive oxygen species at levels which do not substantially impair the physiological activity of the treated blood component comprise the addition of an oxygen scavenger.

3. A method according to claim 2 further comprising selectively removing any unreacted psoralen(s) or photobreakdown products thereof by ultrafiltration of dialysis.

4. A method according to claim 1, wherein at least two psoralens are present.

5. A method according to claim 1, wherein said component is immunoglobin.

6. A method according to claim 1, wherein said blood component is red cells.

7. A method according to claim 1, wherein said blood component is a clotting factor.

8. A method according to claim 1, wherein said blood component is platelets.

9. A method according to claim 1, wherein said blood component is plasma.

10. A method according to claim 1, wherein said psoralen has at least one substituent which is alkyl of from 1 to 3 carbon atoms, alkoxy of from 1 to 3 carbon atoms, or substituted aklyl of from 1 to 6 carbon atoms having 1 to 2 heteroatoms which are oxy or amino.

11. A method according to claim 1, wherein said psoralen has at least one substituent which is alkoxy of from 1 to 3 carbon atoms.

12. A method according to claim 11, wherein said psoralen is 5-methoxypsoralen (5-MOP), 8-methoxypsoralen (8-MOP) or 4'-methoxymethyl-4,5',8-trimethylpsoralen.

13. A method according to claim 1, wherein said psoralen has at least one substituent which is alkyl of from 1 to 3 carbon atoms.

14. A method according to claim 13, wherein said psoralen is 4,5',8-trimethylpsoralen (TMP), 4-methylpsoralen, 4,4'-dimethylpsoralen, 4,5'-dimethylpsoralen or 4',8-dimethylpsoralen.

15. A method according to claim 1, wherein said psoralen has at least one substituent which is alkyl of from 1 to 6 carbon atoms having from 1 to 2 heteroatoms which are oxy or amino.

16. A method according to claim 15, wherein said psoralen is 4'-hydroxymethyl-4,5',8-trimethylpsoralen (HMT) or 4'-aminomethyl-4,5',8-trimethylpsoralen (AMT).

17. A method for decontaminating blood components suspected of containing viruses, said blood components being selected from the group consisting of red blood cells, platelets, blood clotting factors, plasma and immunoglobulins, without substantial impairment of the physiological activity of the treated blood components, said method comprising:
(a) adding to a blood component selected from the group consisting of red blood cells, platelets, blood clotting factors, plasma and immunoglobulins at least one psoralen compound in a total psoralen concentration of at least 1 ug/ml and not more than 300 ug/ml; and thereafter
(b) passing said psoralen treated blood component through a light beam with a wavelength in the range of 300 nm to 400 nm at an intensity of about 0.1 mw/cm$^2$ to 5 W/m$^2$ at a depth of at least 0.025 mm for a total radiation time of about 5 minutes to about 12 hours, wherein said irradiation is conducted under operating conditions which maintain the concentrations of reactive oxygen species at levels which do not substantially impair the physiological activ of the treated blood component.

18. A method according to claim 17 wherein the conditions which maintain the concentrations of reactive oxygen species at levels which do not substantially impair the physiological activity of the treated blood component comprise the addition of an oxygen scavenger.

19. A method according to claim 18 further comprising selectively removing any unreacted psoralen(s) or photobreakdown products thereof by ultrafiltration or dialysis.

20. A method according to claim 17, wherein at least two psoralen are present.

21. A method according to claim 17, wherein said blood component is red cells.

22. A method according to claim 17 wherein said blood commponent is platelets.

23. A method according to claim 17 wherein said blood component is plasma.

24. A method according to claim 17 wherein said blood component is a clotting factor.

25. A method according to claim 17 wherein said blood component is an immunoglobin.

26. A method according to claim 17, wherein said psoralen has at least one substituent which is alkyl of from 1 to 3 carbon atoms, alkoxy of from 1 to 3 carbon atoms, or substituted alkyl of from 1 to 6 carbon atoms having 1 to 2 heteroatoms which are oxy or amino.

27. A method according to claim 17, wherein said psoralen has at least one substituent which is alkoxy of from 1 to 3 carbon atoms.

28. A method according to claim 27, wherein said psoralen is 5-methoxypsoralen (5-MOP), 8-methoxypsoralen (8-MOP) or 4'-methoxymethyl-4,5',8-trimethylpsoralen.

29. A method according to claim 17, wherein said psoralen has at least one substituent which is alkyl of from 1 to 3 carbon atoms.

30. A method according to claim 29, wherein said psoralen is 4,5',8-trimethylpsoralen (TMP), 4-methylpsoralen, 4,4'-dimethylpsoralen, 4,5'-dimethylpsoralen or 4',8-dimethylpsoralen.

31. A method according to claim 17, wherein said psoralen has at least one substituent which is alkyl of from 1 to 6 carbon atoms having from 1 to 2 heteroatoms which are oxy or amino.

32. A method according to claim 31, wherein said psoralen is 4'-hydroxymethyl-4,5',8-trimethylpsoralen (HMT) or 4'-aminomethyl-4,5',8-trimethylpsoralen (AMT).

* * * * *